US006548639B1

(12) United States Patent
Frykberg et al.

(10) Patent No.: US 6,548,639 B1
(45) Date of Patent: Apr. 15, 2003

(54) IGG-BINDING PROTEIN FROM STAPHYLOCOCCUS AND NUCLEOTIDE SEQUENCE ENCODING THIS PROTEIN

(75) Inventors: Lars Frykberg, Uppsala (SE); Karin Jacobsson, Uppsala (SE)

(73) Assignee: Biostapro AB, Stockholm (SE)

( * ) Notice: Subject to any disclaimer, the term of this patent is extended or adjusted under 35 U.S.C. 154(b) by 0 days.

(21) Appl. No.: 09/554,080

(22) PCT Filed: Nov. 11, 1998

(86) PCT No.: PCT/SE98/02036
§ 371 (c)(1),
(2), (4) Date: May 12, 2000

(87) PCT Pub. No.: WO99/24467
PCT Pub. Date: May 20, 1999

(30) Foreign Application Priority Data

Nov. 12, 1997 (SE) ................................................ 9704141

(51) Int. Cl.[7] .................................................. C07K 1/00
(52) U.S. Cl. ...................... 530/350; 530/300; 530/363; 530/402; 530/333; 424/184.1; 424/190.1
(58) Field of Search .................................. 530/350, 300, 530/363, 402, 333; 424/184.1

(56) References Cited

U.S. PATENT DOCUMENTS 4,617,266 A  * 10/1986 Fahnestock .................... 435/68
5,831,012 A  * 11/1998 Nilsson et al. ................. 530/350

OTHER PUBLICATIONS

Reeck, Gerald R. et al, Cell, vol. 50,(667), Aug. 28, 1987.*
Lewin, Roger, Science, vol. 237, pp. 1570, 1987.*
Au et al, Biochemical and Biophysical Research Communications, vol. 138(1), Jul. 1986.*
Jonsson, Hans et al, Gene, vol. 143, pp. 85–89, 1994.*
Popplewell, AG et al, Protein Engineering vol. 4(8), pp. 963–970, 1991.*

(List continued on next page.)

*Primary Examiner*—Lynette R. F. Smith
*Assistant Examiner*—Ginny Allen Portner
(74) *Attorney, Agent, or Firm*—Bacon & Thomas (57) ABSTRACT

A recombinant DNA molecule coding for a protein expressed by a *Staphylococcus aureus* bacterium, comprising the nucleotide sequence SEQ ID NO:1 or a homologous sequence, or a partial or homologous sequence of SEQ ID NO:1 coding for a polypeptide fragment comprising at least 15 amino acid residues, is described. Further, a protein expressed by such a bacterium or a polypeptide fragment comprising at least 15 amino acid residues, comprising the amino acid sequence SEQ ID NO:2 binds IgG and apolipoprotein H. Examples of the polypeptide fragments comprise the SEQ ID NO:3 through 6. These proteins and polypeptide fragments may be coupled to an inert carrier or matrix. Vectors comprising such a DNA molecule or the corresponding RNA molecule, and antibodies specifically binding to a polypeptide having an amino acid sequence of SEQ ID NO:4 or SEQ ID NO:6, are also disclosed. The DNA or RNA molecules, the vectors and the antibodies mentioned may all be used in different types of vaccines against Staphylococcal infections. Moreover, a method of isolating and/or purifying apolipoprotein H from a liquid medium, especially from serum, is described.

2 Claims, 4 Drawing Sheets

OTHER PUBLICATIONS

Boslego, JW et al, Chapter 17, Vaccines and Immunotherapy, pp. 211–223.*
Ellis, R.W., Ph.D. Chapter 29, p. 568–574, Vaccines, 1988.*
Jacobsson, K et al, Biotechniques, May 1995, vol. 18(5), apges 878–885.*
Mehdi, H et al, Journal of Virology, vol. 68(4), pp. 2415–2424, Apr. 1994.*
Biotechniques, vol. 18, No. 5, 1995, Karin Jacobsson et al., "Cloning of Ligand–Binding Domains of Bacterial Receptors by Phage Display".
Databas Swissprot:spa2–Staau P38507, Shuttleworth H.L. et al., "Immunoglobulin G binding protein A precursor (protein A)", 1987.
Microbiology, vol. 144, 1998, Lihong Zhang et al., "A second IgG–binding protein in Staphylococcus aureus".

* cited by examiner

Fig. 1

```
AGTACTTCCTTACTTAAAATACGCTGAATGTTCTGAATTAAACGCTTTTTTACATAGTTA            60
ACACTAGTTAATCTATTAGTTAACATTAGTTAATAATTAGTTAATTTCCATTTGTATTCT           120
CATGTGATAAATTCTAAAAGCATACAATAAATTTAATATGTAAAAGAAAGGGAATACAC           180
     ATGAAAAATAAATATATCTCGAAGTTGCTAGTTGGGGCAGCAACAATTACGTTAGCTACA       240
   1 M  K  N  K  Y  I  S  K  L  L  V  G  A  A  T  I  T  L  A  T
     ATGATTTCAAATGGGGAAGCAAAAGCGAGTGAAAACACGCAACAAACTTCAACTAAGCAC       300
  21 M  I  S  N  G  E  A  K  A  S  E  N  T  Q  Q  T  S  T  K  H
     CAAACAACTCAAAACAACTACGTAACAGATCAACAAAAAGCTTTTTATCAAGTATTACAT       360
  41 Q  T  T  Q  N  N  Y  V  T  D  Q  Q  K  A  F  Y  Q  V  L  H
     CTAAAAGGTATCACAGAAGAACAACGTAACCAATACATCAAAACATTACGCGAACACCCA       420
  61 L  K  G  I  T  E  E  Q  R  N  Q  Y  I  K  T  L  R  E  H  P
     GAACGTGCACAAGAAGTATTCTCTGAATCACTTAAAGACAGCAAGAACCCAGACCGACGT       480
  81 E  R  A  Q  E  V  F  S  E  S  L  K  D  S  K  N  P  D  R  R
     GTTGCACAACAAAACGCTTTTTACAATGTTCTTAAAAATGATAACTTAACTGAACAAGAA       540
 101 V  A  Q  Q  N  A  F  Y  N  V  L  K  N  D  N  L  T  E  Q  E
     AAAAATAATTACATTGCACAAATTAAAGAAAACCCTGATAGAAGCCAACAAGTTTGGGTA       600
 121 K  N  N  Y  I  A  Q  I  K  E  N  P  D  R  S  Q  Q  V  W  V
     GAATCAGTACAATCTTCTAAAGCTAAAGAACGTCAAAATATTGAAAATGCGGATAAAGCA       660
 141 E  S  V  Q  S  S  K  A  K  E  R  Q  N  I  E  N  A  D  K  A
     ATTAAAGATTTCCAAGATAACAAAGCACCACACGATAAATCAGCAGCATATGAAGCTAAC       720
 161 I  K  D  F  Q  D  N  K  A  P  H  D  K  S  A  A  Y  E  A  N
     TCAAAATTACCTAAAGATTTACGTGATAAAAACAACCGCTTTGTAGAAAAAGTTTCAATT       780
 181 S  K  L  P  K  D  L  R  D  K  N  N  R  F  V  E  K  V  S  I
     GAAAAAGCAATCGTTCGTCATGATGAGCGTGTGAAATCAGCAAATGATGCAATCTCAAAA       840
 201 E  K  A  I  V  R  H  D  E  R  V  K  S  A  N  D  A  I  S  K
     TTAAATGAAAAAGATTCAATTGAAAACAGACGTTTAGCACAACGTGAAGTTAACAAAGCA       900
 221 L  N  E  K  D  S  I  E  N  R  R  L  A  Q  R  E  V  N  K  A
```

Fig. 2a

```
     CCTATGGATGTAAAAGAGCATTTACAGAAACAATTAGACGCATTAGTTGCTCAAAAAGAT  960
241  P  M  D  V  K  E  H  L  Q  K  Q  L  D  A  L  V  A  Q  K  D

GCTGAAAAGAAAGTGGCGCCAAAAGTTGAGGCTCCTCAAATTCAATCACCACAAATTGAA 1020
261  A  E  K  K  V  A  P  K  V  E  A  P  Q  I  Q  S  P  Q  I  E

AAACCTAAAGTAGAATCACCAAAAGTTGAAGTCCCTCAAATTCAATCACCAAAAGTTGAG 1080
281  K  P  K  V  E  S  P  K  V  E  V  P  Q  I  Q  S  P  K  V  E

GTTCCTCAATCTAAATTATTAGGTTACTACCAATCATTAAAAGATTCATTTAACTATGGT 1140
301  V  P  Q  S  K  L  L  G  Y  Y  Q  S  L  K  D  S  F  N  Y  G

TACAAGTATTTAACAGATACTTATAAAAGCTATAAAGAAAAATATGATACAGCAAAGTAC 1200
321  Y  K  Y  L  T  D  T  Y  K  S  Y  K  E  K  Y  D  T  A  K  Y

TACTATAATACGTACTATAAATACAAAGGTGCGATTGATCAAACAGTATTAACAGTACTA 1260
341  Y  Y  N  T  Y  Y  K  Y  K  G  A  I  D  Q  T  V  L  T  V  L

GGTAGTGGTTCTAAATCTTACATCCAACCATTGAAAGTTGATGATAAAAACGGCTACTTA 1320
361  G  S  G  S  K  S  Y  I  Q  P  L  K  V  D  D  K  N  G  Y  L

GCTAAATCATATGCACAAGTAAGAAACTATGTAACTGAGTCAATCAATACTGGTAAAGTA 1380
381  A  K  S  Y  A  Q  V  R  N  Y  V  T  E  S  I  N  T  G  K  V

TTATATACTTTCTACCAAAACCCAACATTAGTAAAAACAGCTATTAAAGCTCAAGAAACT 1440
401  L  Y  T  F  Y  Q  N  P  T  L  V  K  T  A  I  K  A  Q  E  T

GCATCATCAATCAAAAATACATTAAGTAATTTATTATCATTCTGGAAATAATCAATCAAA 1500
421  A  S  S  I  K  N  T  L  S  N  L  L  S  F  W  K

AATATCTTCTCTAGTTTTACATCATTTTTTAAATAATTTTCGTAACAAACCGTGATTAAA 1560

AAGAACCGTTGATTCTCAATCGAATCTACGGTTCTTTTTTCATTTTCCATCAATTAAATG 1620
```

IGG-BINDING PROTEIN FROM STAPHYLOCOCCUS AND NUCLEOTIDE SEQUENCE ENCODING THIS PROTEIN

The present invention relates to a new protein and a nucleotide sequence encoding said protein. More precisely, the invention relates to a DNA molecule coding for a protein expressed by a bacterium of the genus *Staphylococcus aureus*, said protein and polypeptide fragments of said protein. Vectors comprising the nucleotide sequence coding for the protein, the protein and fragments thereof, and antibodies specifically binding to the protein may all be used for different vaccines against Staphylococcal infections in mammals. The invention also relates to a method of isolating and/or purifying apolipoprotein H from e.g serum with an immobilised protein or polypeptide of the invention.

BACKGROUND OF THE INVENTION

*Staphylococcus aureus* is a pathogen responsible for a wide variety of diseases in humans and animals, including endocarditis, osteomyelitis, wound sepsis and mastitis. The bacterium produces several potential virulence factors such as alpha-, beta-, gamma- and delta-toxins, toxic shock syndrome toxin (TSST), enterotoxins, leucocidin, proteases, coagulase and clumping factor.

It is generally accepted that adhesion to tissues is required for bacterial colonisation to occur. For this purpose staphylococci express surface adhesins, which interact with host matrix proteins such as fibronectin, vitronectin, collagen, laminin and bone sialoprotein. In addition, staphylococci are able to bind several serum proteins, such as IgG, fibronectin, fibrinogen, and thrombospondin, possibly masking the bacteria from the immune system of the host. However, the contribution and importance of each of these binding functions in different infections is still unclear.

The most studied receptor in *S. aureus* is protein A, a cell wall-associated protein, which binds to the Fc- and the Fab-regions of IgG from several species. Protein A in strain 83254 consists of five consecutive, highly homologous domains, all with IgG-binding activity, followed by a region anchoring the protein in the cell wall (Uhlén et al, 1984). IgG-binding ability is common among clinical strains of *S. aureus* suggesting an important function in pathogenesis. It has been assumed that the IgG-binding capacity is mediated by protein A only.

However, the present inventors recently identified a nucleotide sequence in *S. aureus* strain 8325-4 encoding a polypeptide, clearly distinguishable from protein A, which binds IgG in a non-immune fashion (Jacobsson & Frykberg, 1995). An IgG-binding protein fragment having an amino acid sequence of 84 aa was disclosed. However, the amino acid sequence of the full length protein and the properties other than the IgG-binding ability of the 84 aa fragment were not known or even suggested. No nucleotide sequence coding for said protein has be disclosed or suggested prior to the present invention.

Diseases caused by Staphylococcal infections are often treated with antibiotics. As is well known in the art, these microorganisms can develop antibiotic resistance. Therefore, the use of vaccines to prevent or contain the spread of infection would be desirable. At present, there is no vaccine on the market that gives full protection. The present invention provides new immunologically active components for the production of vaccines against Staphylococcal infections.

DESCRIPTION OF THE INVENTION

The present invention is based on cloning and nucleotide sequence determination of a complete gene (sbi) encoding a novel IgG-binding protein. The gene encodes a protein of 436 amino acids, denoted protein Sbi, with one IgG-binding domain that exhibits an immunoglobulin-binding specificity similar to protein A and without the typical Gram-positive cell wall anchoring sequence LPXTG (SEQ ID NO:7) (Schneewind et al, 1995) suggesting that the protein is not anchored in the cell wall. Analysis of other *S. aureus* strains shows that this gene is not unique for strain 8325-4. For instance, the Sbi-protein is highly expressed in strain Newman 4, which shows that the IgG-binding activity observed in *S. aureus* is not mediated only by protein A. In fact, this (sbi) gene is present in all tested strains of *S. aureus*.

Further, it has now been revealed that the Sbi protein of the invention binds apolipoprotein H, a major serum component, in addition to IgG. Hitherto, no bacterial protein binding to apolipoprotein H has been reported. Therefore, neither is this combination of the protein binding to these two serum components previously known. The portion of the protein which binds to IgG is located near the N-terminal of the protein, whereas the middle portion binds to apolipoprotein H. This enables the use of the protein, or an appropriate polypeptide fragment, in immobilised form for the isolation and/or purification of apolipoprotein H.

Thus, one aspect of the present invention is directed to a recombinant DNA molecule coding for a protein expressed by a bacterium of the genus *Staphylococcus aureus*, comprising the nucleotide sequence SEQ ID NO:1, defined in the sequence listing and the claims, or a homologous sequence to SEQ ID NO:1 coding for said protein, or a partial or homologous sequence of the sequence SEQ ID NO:1 coding for a polypeptide fragment of said protein comprising at least 15 amino acid residues.

This recombinant DNA molecule may be inserted into plasmids, phages or phagemides for the expression/production of the protein or protein fragments.

Another aspect of the invention is directed to a protein expressed by a bacterium of the genus *Staphylococcus aureus* or a polypeptide fragment of said protein comprising at least 15 amino acid residues other than the 84 aa fragment at the position 38-121, which protein comprises the amino acid sequence SEQ ID NO:2, defined in the sequence listing and the claims, or a homologous sequence to the sequence SEQ ID NO:2 comprising a few mismatches in the amino acid sequence of SEQ ID NO:2, or polypeptide fragments of said homologous sequence comprising at least 15 amino acid residues.

The disclaimer of the 84 aa fragment at the position 38-121 of the SEQ ID NO:2 is made because, as already mentioned, it has been previously disclosed (Jacobsson & Frykberg, 1995).

It is well known in the art that there may be a few mismatches of amino acids residues in the amino acid sequence of a protein while the protein still retains its major characteristics. The mismatches may be replacements of one or several amino acids, deletions of amino acid residues or truncations of the protein. Such mismatches occur frequently in genetic variations of native proteins. It is believed that up to 15% of the amino acid residues may be replaced in a protein while the protein still retains its major characteristics. The protein of the invention comprises 436 amino acid residues, and therefore up to 66 mismatches would be acceptable. However, preferably there will be less than 20, more preferably less than 10, and most preferably less than 5 mitsmatches in the amino acid sequence of the protein of the invention.

The polypeptide fragments of the protein of the invention should comprise at least 15 amino acid residues to be sure that the fragments are not found in other known proteins. These fragments may be used e.g. as probes, diagnostic antigens, and vaccine components, possibly coupled to carriers.

In an embodiment of this aspect of the invention a polypeptide fragment of the protein according to the invention has the amino acid sequence SEQ ID NO:3, defined in the sequence listing and the claims. This polypeptide fragment lacks the signal sequence of the SEQ ID NO:1.

In another embodiment a polypeptide fragment of the protein according to the invention has an amino acid sequence SEQ ID NO:4, defined in the sequence listing and the claims. This polypeptide fragment binds apolipoprotein H.

In yet another embodiment a polypeptide fragment of the protein according to the invention has the amino acid sequence SEQ ID NO:5, defined in the sequence listing and the claims. This 120 aa polypeptide fragment binds IgG. It was chosen for immunisation purposes, in stead of the known IgG binding 84 aa fragment, since once the whole amino acid sequence was deduced, it became evident there were sequence similarities suggesting two IgG binding domains.

In still another embodiment a polypeptide fragment of the protein according to the invention has the amino acid sequence SEQ ID NO:6. This polypeptide fragment binds apolipoprotein H, and has been used for isolation and purification of said serum protein.

In a preferred embodiment of this aspect of the invention the protein or polypeptide according to the invention is coupled to an inert carrier or matrix. The carrier may be e.g. plastic surfaces, such as microplates, beads etc.; organic molecules such as biotin; proteins, such as bovine serum albumin; peptide linkers, polypeptides e.g. resulting in fusion proteins. The matrix may be particles used for chromatographic purposes, such as Sepharose®.

A further aspect of the invention is directed to a vector selected from the group consisting of plasmids, phages or phagemides comprising a nucleotide sequence according to the invention.

These vectors may be used for the production of the proteins or polypeptides of the invention. They may also be used in vaccines.

Yet another aspect of the invention is directed to antibodies specifically binding to a polypeptide having an amino acid sequence selected from the group consisting of SEQ ID NO:4, and SEQ ID NO:6. The specific binding of binding of an antibody to an amino acid sequence of the invention requires e.g an affinity constant of at least $10^7$ liters/mole, preferably at least $10^9$ liters/mole.

The antibodies of the invention may be monoclonal or polyclonal. They may be used in diagnostic tests, but preferably in vaccines for passive immunization.

Still another aspect of the invention is directed to the use of a protein or polypeptide according to the invention, optionally in immobilised form, as an immunising component in the production of a vaccine against Staphylococcus infections.

Another use aspect of the invention is directed to the use of a vector according to the invention for the production of a vaccine against Staphylococcal infections.

Yet another use aspect of the invention is directed to the use of antibodies according to the invention for the production of a vaccine for the passive immunisation of a mammal against Staphylococcus infections.

An additional aspect of the invention is directed to a vaccine against Staphylococcal infections comprising as an immunising component a protein or polypeptide according to the invention, optionally in immobilised form.

Another vaccine aspect of the invention is directed to a vaccine against Staphylococcal infections comprising a vector according to the invention.

A DNA molecule, or the corresponding RNA derived from the present sequence, as described in claim 1, may be used in a vector for vaccine purposes. Examples of suitable forms of administration include intravenous, percutaneous, and intramuscular administration.

Yet another vaccine aspect of the invention is directed to a vaccine for the passive immunisation of a mammal, especially a human being, against Staphylococcus infections comprising antibodies according to the invention.

One embodiment of the invention comprises the passive immunization of patients with an impaired immune defense or patient awaiting major surgery, such as patients in line for an organ transplantation or awaiting the insertion of a prosthetic device, such as a hip prosthesis or similar major surgical intervention. According to the present invention, a high dose of antibodies against the novel protein can be administered to any patient before or at the time of hospitalisation, in order to prevent Staphylococcus infection.

The vaccines may contain other ingredients selected with regard to the intended administration rout, and these ingredients are chosen by the vaccine manufacturer in collabaration with pharmacologists. Examples of administration routs include intravenous administration, percutaneous administration, oral and nasal administration.

A further aspect of the invention is directed to a method of prophylactic and/or therapeutic treatment of Staphylococcus infections in a mammal comprising administration to said mammal of an immunologically effective amount of a vaccine according to any one of the vaccines of the invention.

Still another aspect of the invention is directed to a method of isolating and/or purifying apolipoprotein H from a liquid medium, especially from serum, comprising chromatographic separation of apolipoprotein H from said liquid medium with an immobilised protein or polypeptide according to the invention as stationary phase.

In a preferred embodiment of the invention column chromatography is used for the isolation/purification of apolipoprotein H from blood serum. The protein or polypeptide of the invention is coupled to e.g. Sepharose® and is used as packing material for the column. The apolipoprotein H-containing serum is brought into contact with the immobilized protein or polypeptide and the apolipoprotein H is adsorbed. Finally, the apolipoprotein H is eluated from the column.

DESCRIPTION OF THE DRAWINGS

FIGS. 2*a*+2*b* show the complete nucleotide sequence of the sbi-gene (SEQ ID NO:1) of the invention from *S. aureus*

8325-4, and the deduced amino acid sequence of the encoded protein. Features of the sequence are indicated as follows: underbar, putative promotor sequences; double underbar, possible ribosomal binding site; overbar, putative transcriptional stop signal (inverted repeat); single vertical arrow indicates the cleavage site of the signal sequence and in bold the repeated proline residues. Also shown in bold is the minimal IgG- binding domain as deduced by shot gun phage display mapping.

EXPERIMENTS

Analysis of IgG binding activity in *S. aureus* by Western blots usually reveals more than one protein band, which interact with IgG, and it has been assumed that these polypeptides represent breakdown products of protein A. In view of the present results, it is not surprising that protein Sbi has escaped detection. For example, analysis of the expression of the protein Sbi in *S. aureus* has been hampered by the ability of protein A to interact with IgGs from most mammalian species. Furthermore, both proteins migrate similarly in SDS-PAGE and have the same specificity for all tested immunoglobulins. As disclosed in Example 4 below, the commercially available anti-protein A antibodies cross-react with full-length protein Sbi but not with MAL-SbiΔ (SEQ ID NO:4) (lacking the known IgG-binding domain). Most likely, the cross-reaction is not unique to this source of antibodies and may have contributed to the failure to identify protein Sbi. Now the antibodies directed against the protein Sbi of the invention produced in chicken allows discrimination between expression of protein A and protein Sbi.

The present inventors have cloned and sequenced the sbi-gene from *S. aureus* strain 8325-4. The detection of protein Sbi, expressed from its own promoter in *S. epidermidis* and as a MAL-fusion in *E. coli* with HRP-labelled IgG, proves that this gene encodes a second IgG-binding protein. This protein consists of 436 amino acids (SEQ ID NO:2) and contains a signal sequence but lacks the cell wall sorting LPXTG (SEQ ID NO:7) motif, suggesting that the protein is not anchored in the cell-wall. However, in strain Newman 4, which produces high amounts of protein Sbi, no protein Sbi is detected in the culture growth medium (data not shown). Instead, protein Sbi is released from the cell surface by addition of sample buffer (Example 4), in contrast, release of protein A requires treatment with lysostaphin (Example 4). This indicates that protein Sbi is associated to the cell surface by a different mechanism. There are also other examples of cell surface associated proteins that lack the LPXTG motif, such as the *S. aureus* elastin-binding protein (Park et al 1996) and MHC class II analogue (Jönsson et al 1995).

Mapping of protein Sbi by shot-gun phage display strongly suggests that the protein has only one IgG-binding domain with a deduced minimal binding domain of 52 amino acids. Furthermore, expression and analysis of $NH_2$-terminally truncated Sbi-protein, i.e. the C-terminal part of the protein, consisting of aa 143–436 ( SEQ ID NO:4), shows that no IgG-binding activity is located in this part of the protein (Example 4). The IgG-binding domain shows a significant homology to the IgG-binding repeats of protein A (FIG. 3).

Figure 1:
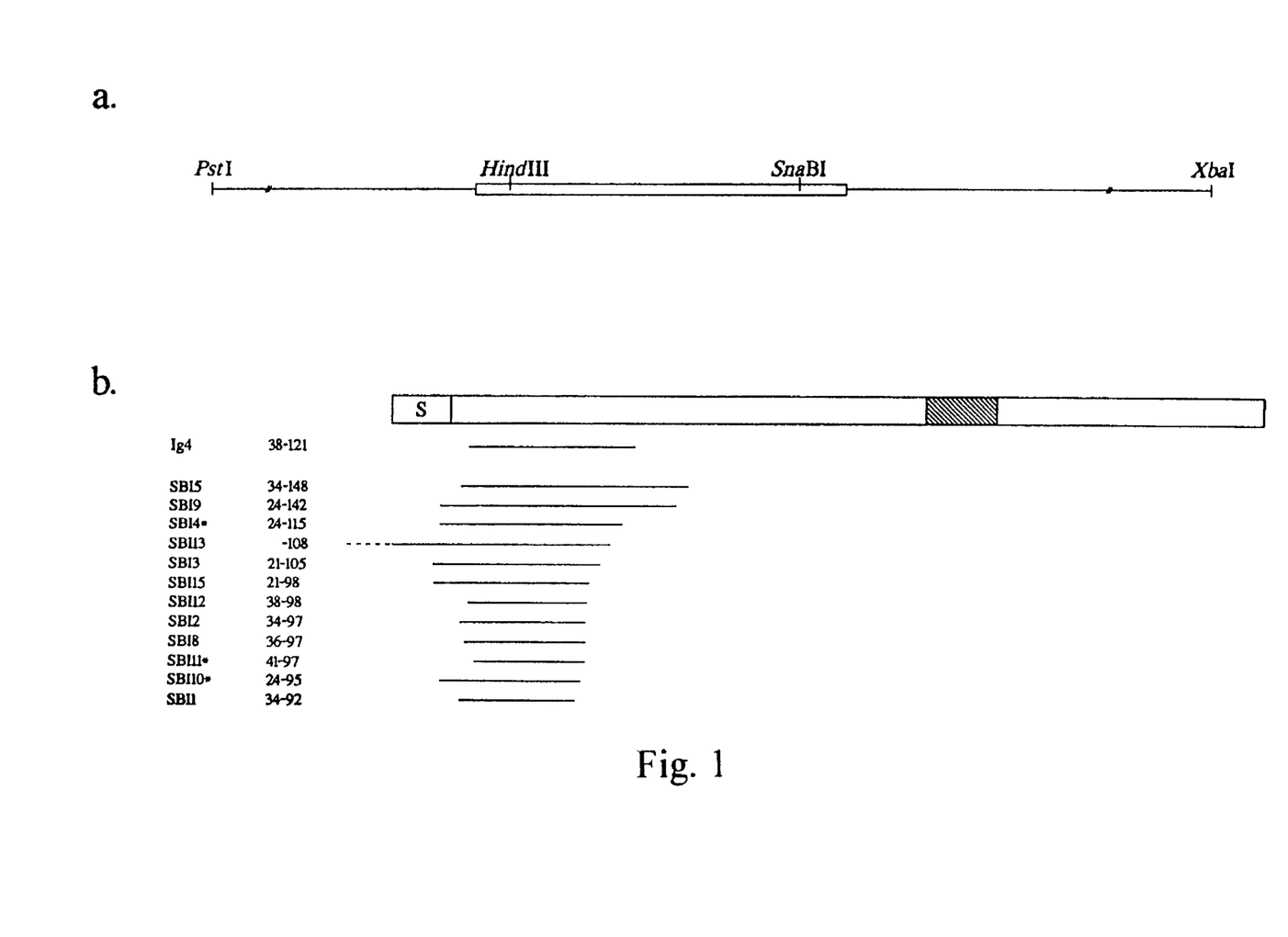
FIG. 1 shows a) the cloned 3 kb PstI-XbaI fragment from *S. aureus* strain 8325-4 containing the sbi-gene of the invention (clone pPX1), and b) schematic drawing of the protein Sbi aligned with the peptides encoded by the phagemid clones isolated by panning against IgG. Stars indicate that the clone was isolated several times independently. Ig4 represents the clone isolated earlier (Jacobsson & Frykberg, 1995). S denotes the signal sequence and the shaded bar represents a proline-rich region.
Figure 3:
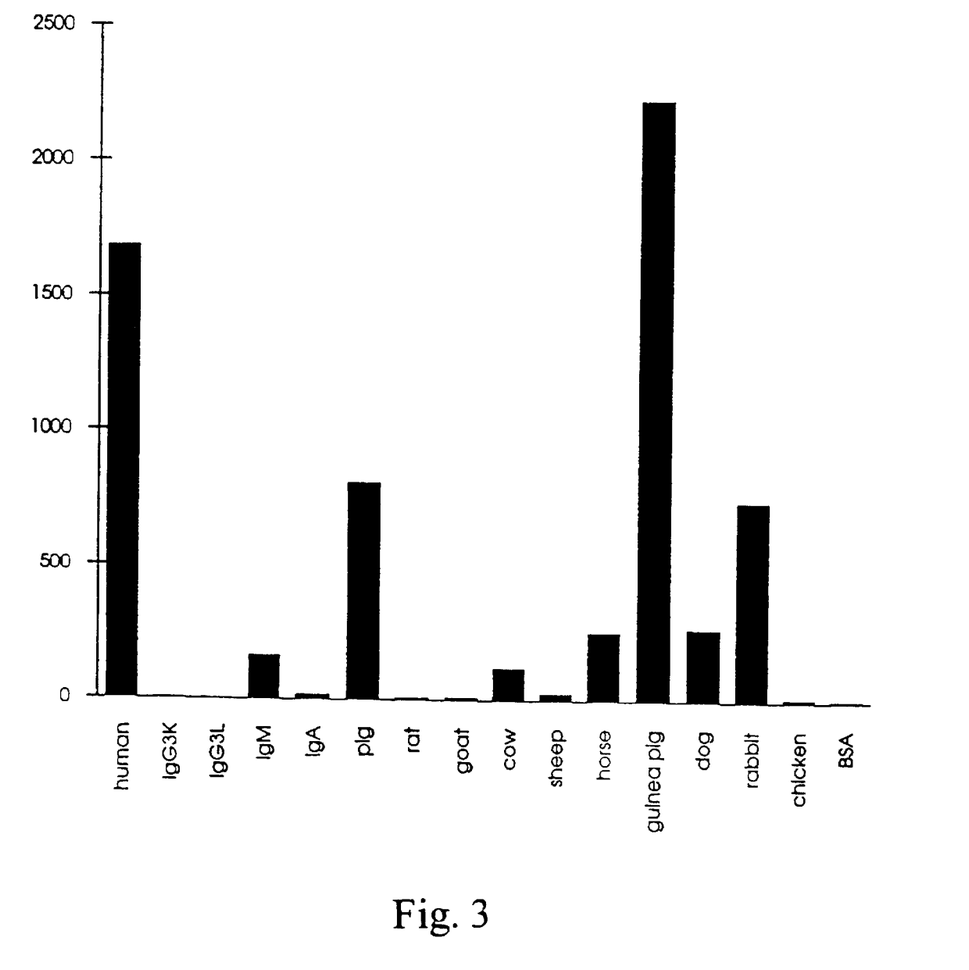
FIG. 3 shows the specificity of the binding domain of the protein Sbi (clone Ig4) for various IgGs and human IgG3κ, IgG3λ, IgM and IgA. Each column represents a mean value of two independent experiments with the same phage stock. The y-axis shows the number of c.f.u. in 50 μl of the eluate.

A phage-stock made from the originally isolated clone, Ig4 (aa 38–121) (FIG. 1b), was used in an analysis of the immunoglobulin species reactivity (FIG. 3). A comparison between data on the specificity of protein A (Boyle, 1990) and the results for clone Ig4 (FIG. 3) shows, that the two proteins exhibit a very similar Ig-binding profile. In addition, a study using one or two binding domains from protein A (clones Ig7 (domain C) and Ig1 (D-A) described by Jacobsson & Frykberg (1995)) gave an Ig-binding profile similar to that of Ig4 (data not shown). The display of protein domain(s) on the phage surface offers a quick and sensitive method for analysing specific binding to other molecules.

Further, the present protein has been shown to bind to another serum protein, apolipoprotein H, also known as β2-glycoprotein I. Hitherto, no bacterial protein binding to apolipoprotein H has been reported. This finding is unexpected and opens new possibilities to use the protein for isolation/purification of apolipoprotein H for research laboratories and for the production of antibodies against the apolipoprotein H binding portion of the protein. These antibodies may be used as components in vaccines for passive immunisation of mammals against Staphylococcus infections.

EXAMPLES

Bacterial Strains Growth Conditions, Vectors and Helper Phage

The bacterial strains used are listed in Table 1. Phage R408 (Promega) was used as the helper phage for production of phage stocks. *E. coli* containing the pUC18 or pMAL-c2 vectors (New England Biolabs) were selected on LA-plates (Luria-Bertani (LB)-broth with 1.5% agar and 50 μg ampicillin $ml^{-1}$) and grown in LB-broth supplied with 50 μg ampicillin $ml^{-1}$. *E. coli* containing the phagemid vector pHEN1 (Hoogenboom et al, 1991), were grown in the same medium supplemented with 1% glucose (w/v). Staphylococcal strains were grown in Tryptone Soya Broth (TSB) (Oxoid). *S. epidermidis* containing pBR473 was grown in the same medium containing 20 μg $ml^{-1}$ of chloramphenicol.

TABLE 1

| Bacterial strains | | |
|---|---|---|
| Species | Strain | Characteristics and use |
| *E. coli* | TG1 | $F^+$ and amber suppressing. Used for construction of the phage library and production of phage stocks. |
|  | MC1061 | Used for all other DNA manipulations. |
| *S. aureus* | 8325-4 | NCTC 8325 cured from prophages |
|  | Wood 46 | Protein A-negative reference strain |
|  | Newman 4 | Spontaneous mutant of strain Newman with enhanced production of fibronectin-binding protein |
|  | Cowan I | NCTC 8350, high level producer of cell-wall-bound protein A. |
| *S. epidermidis* | 247 |  |

Example 1

Cloning and Sequencing of the sbi Gene Encoding an IgG-binding Protein

Restriction and modification enzymes were purchased from Promega, Amersham International, or Boehringer Mannheim. Oligonucleotides were synthesized by Scandinavian Gene Synthesis AB or Pharmacia Biotech and are listed in Table 2.

TABLE 2

Oligonucleotides.

| Name | Use | Sequence |
|---|---|---|
| Pe | Sequencing of pHEN1 clones | 5'-TTG CCT ACG GCA GCC GCT GAA-3' (SEQ ID NO:8) |
| My | Sequencing of pHEN1 clones | 5'-TGC GGC CCC ATT CAG ATC CTC-3' (SEQ ID NO:9) |
| Olg1 | Sequencing of sbi | 5'-CTC CAT ATA GTA CTT CCT TA-3' (SEQ ID NO:10) |
| Olg2 | Sequencing of sbi | 5'-GAG ATT GCA TCA TTT GCT GA-3' (SEQ ID NO:11) |
| Olg3 | Sequencing of sbi | 5'-GTA ACC ATA GTT AAA TGA AT-3' (SEQ ID NO:12) |
| Olg4 | Sequencing of sbi | 5'-CGA TAA ATC AGC AGC ATA TG-3' (SEQ ID NO:13) |
| Olg5 | Sequencing of sbi | 5'-CAA TCA CCA CAA ATT GAA AA-3' (SEQ ID NO:14) |
| Olg6 | Sequencing of sbi | 5'-TGG TGC TTG TAG TGG AAA AG-3' (SEQ ID NO:15) |
| Olg8 | PCR for MAL-E fusions | 5'-AGT GGA TCC ACG CAA CAA ACT TCA ACT AAG CA-3' (SEQ ID NO:16) |
| Olg9 | PCR for MAL-E fusions and constr. of sbi-probe | 5'-AAT GTC GAC AAA CTA GAG AAG ATA TTT TTG A-3' (SEQ ID NO:17) |
| Olg10 | PCR for MAL-E fusions and constr. of sbi-probe | 5'-TAG GAT CCG TAC AAT CTT CTA AAG CTA AAG A-3' (SEQ ID NO:18) |

All DNA manipulations were performed using standard methods (Sambrook et al, 1989), except ligations and small scale plasmid preparations, for which the Ready to Go-ligation kit (Pharmacia Biotech) and Wizard™ Miniprep DNA Purification systems (Promega), respectively, were used according to the manufacturers' instructions. Plasmids were introduced into *E. coli* and staphylococci by electrotransformation. Staphylococcal chromosomal DNA was prepared according to Lindberg et al (1972).

DNA was sequenced according to the dideoxy chain termination method using the Sequenase® version 2.0 DNA sequencing kit from United States Biochemical. Restriction sites shown in FIG. 1 were used for construction of subclones used in determination of the nucleotide sequence. One additional clone, pHSBB7, was made (not shown) by Bal31 exonuclease digestion from the unique HindIII site in the 3' direction of the gene, and sequenced. Different oligonucleotides were used as primers for determining the sequence of both DNA strands (Table 2). The PC-gene program (Intelligenetics) was used for the handling of the sequences. The EMBL, GeneBank, SWISS-protein and PIR databases were searched for sequence-homologies.

To express the Sbi protein, two constructs were made in the pMAL-c2-vector. Primers Olg8 and 9 were used to PCR-amplify the DNA encoding full-length protein lacking the signal sequence (aa 33–436, SEQ ID NO:3). Primers Olg9 and 10 were used to PCR-amplify the DNA encoding a truncated version (aa 143–436, SEQ ID NO:4) lacking also the known IgG-binding domain. The obtained PCR-products were digested with the restriction enzymes BamHI and SalI and ligated into the vector cleaved with the same enzymes and transformed into *E. coli*.

Southern blots and hybridizations were performed according to Sambrook et al (1989), using a NcoI-XhoI fragment, i.e. the complete insert from clone Ig4, (Jacobsson & Frykberg, 1995) $^{32}$P-labelled by random priming for detection and cloning of the sbi-gene. For detection of the sbi-gene in different *S. aureus* strains, the PCR-fragment obtained by using Olg9 and 10 (see above) was $^{32}$P-labelled by random-priming. The hybridisation was carried out at 50° C. and the washing at 65° C. in 0.1×SSC (20×SSC=3.0M NaCl and 0.3M Na-citrate) and 0.1% SDS.

The original clone (FIG. 1b, clone Ig4) expressing an IgG-binding polypeptide was earlier isolated from a shotgun phage display library made from *S. aureus* strain 8325-4 (Jacobsson & Frykberg, 1995). The insert from this clone was used as a probe for identification and subsequently for cloning of the complete gene from *S. aureus* strain 8325-4. Chromosomal DNA was digested with PstI and XbaI, and the DNA fragments were separated by agarose gel electrophoresis followed by blotting onto a nitrocellulose filter. Hybridization with the NcoI-XhoI fragment, derived from Ig4, showed that the gene of the invention resided on a fragment of approximately 3 kb in size. DNA fragments of this size were purified by agarose gel electrophoresis and cloned into the pUC18 vector. One clone, pPX1, hybridizing with the probe was further characterized by restriction enzyme analysis. FIG. 1 schematically shows the 3 kb PstI-XbaI DNA fragment containing the sbi-gene and the different restriction enzymes used for subcloning.

Figure 2A:
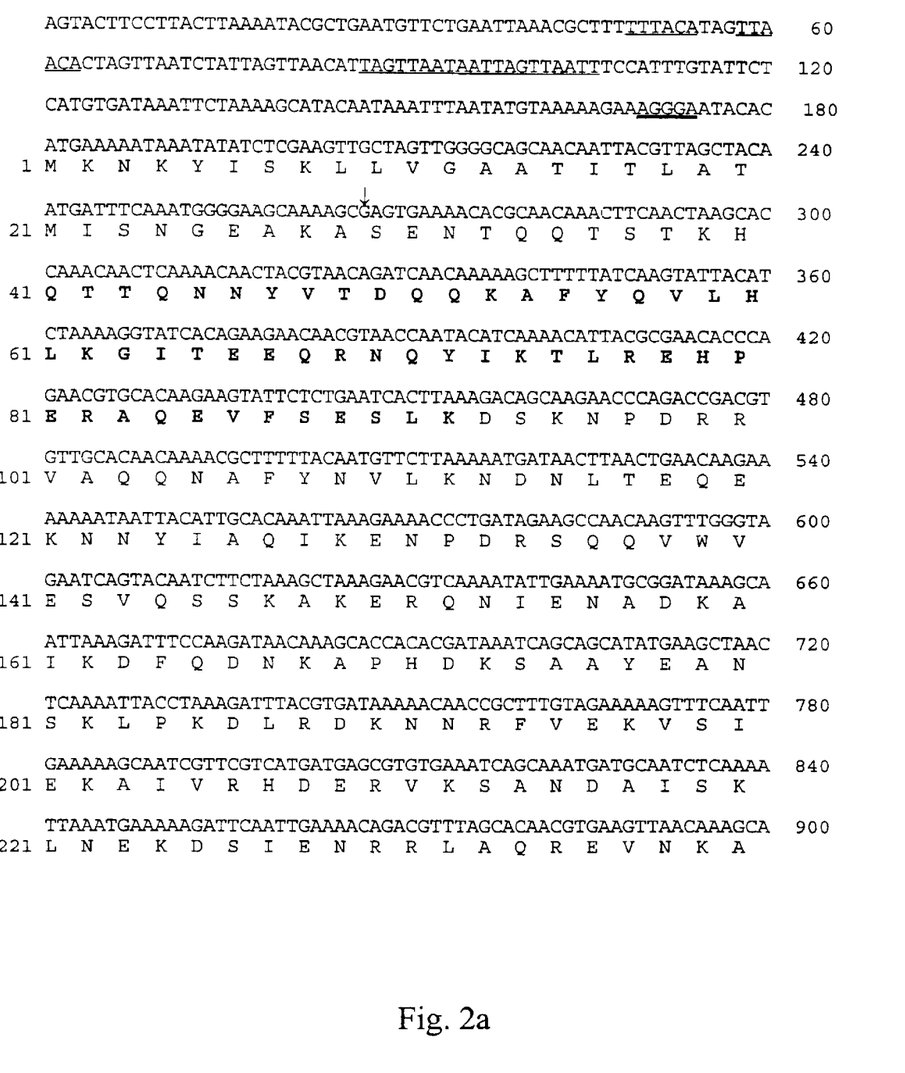
Figure 2B:
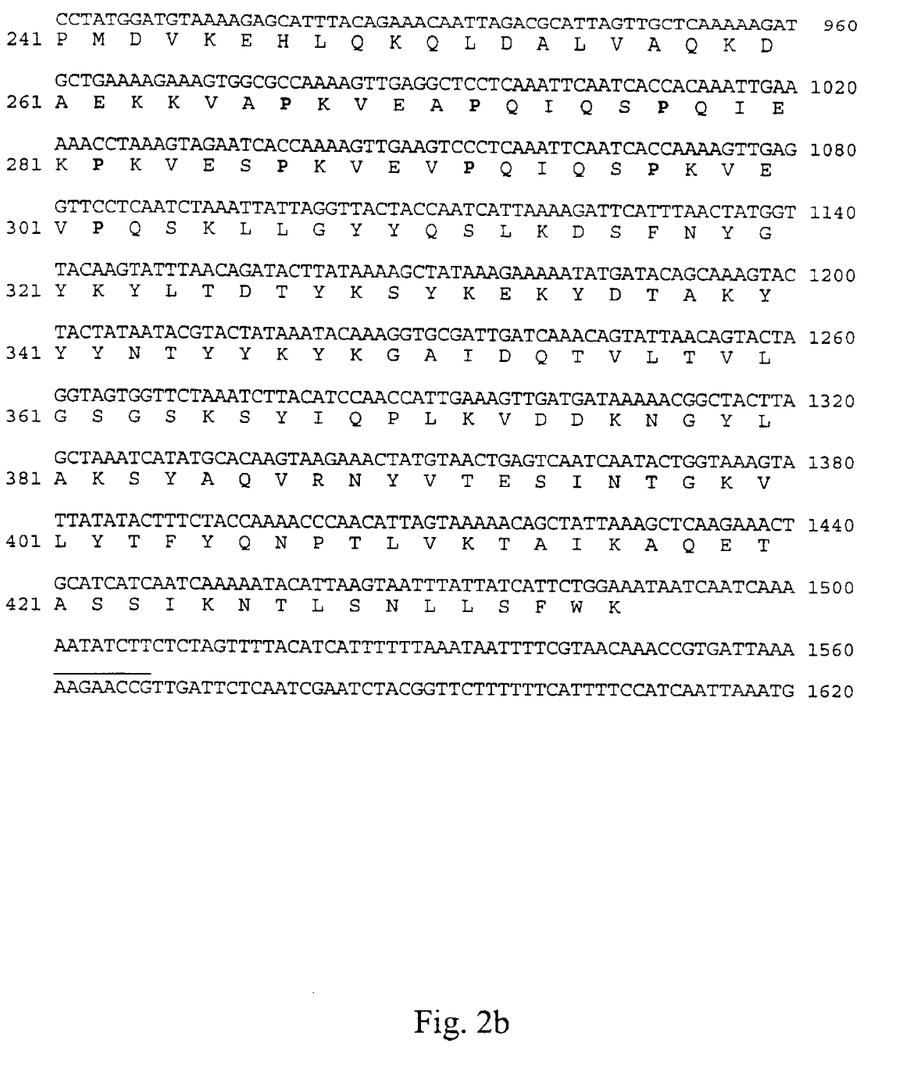

FIG. 2 shows 1620 nt of the 3 kb PstI-XbaI DNA fragment. The coding sequence starts with a Met at nucleotide position 181 and ends with a stop codon at position 1488 (SEQ ID NO:1), encoding a protein of 436 amino acids (SEQ ID NO:2), including a typical signal peptide with a putative cleavage site after amino acid 29. The gene has the normal features associated with a functional gene, putative promotor sequences, a possible ribosomal binding site and an inverted repeat located after the translation termination stop codon. A proline rich sequence, containing eight prolines repeated every fifth amino acid, starts at position 267. Such sequences are normally found within cell wall spanning domains. However, in this case the proline rich region is not followed by the cell wall sorting LPXTG motif (Schneewind et al, 1995).

Example 2

Mapping of the IG-binding Domain in Protein Sbi

The library was constructed from the cloned sbi-gene essentially as described (Jacobsson 10 & Frykberg, 1995). In short, the DNA from clone pPX1 (FIG. 1a) was sonicated and DNA fragments in size of approximately 50–300 bp were isolated by preparative gel electrophoresis. The fragments were blunt-ended with T4 DNA polymerase and ligated into the phagemid pHEN1, previously digested with Pst1, made blunt-ended, and dephosphorylated with calf intestine alkaline phosphatase. The ligation was made using 1 μg of vector and 1 μg of DNA fragments and the mixture was transformed into *E. coli* TG1. The transformants were grown over night in LB supplied with 50 μg ampicillin ml$^{-1}$ and 1% glucose (w/v) and thereafter infected with helper phage R408 at a MOI of 20. After 1 hour the culture was diluted and ampicillin added to a final concentration of 50 μg ml⁻¹. After 5 hours of growth at 37° C., the bacteria were pelletted and the supernatant, containing the phages, was sterile filtered.

The library was affinity selected against human IgG (Kabivitrum) and positive clones were identified using labelled IgG as described (Jacobsson & Frykberg, 1995).

In order to determine the exact position of the IgG-binding domain in protein Sbi a shot-gun phage display library was made from clone pPX1. After panning the library against immobilized human IgG, E. coli TG1 cells were infected with the eluted phage and the bacteria were spread on LA-plates containing ampicillin. Amp$^R$ colonies were analysed for binding of HRP-labelled human IgG. Positive clones were isolated and the nucleotide sequences of the different inserts were determined. As seen in FIG. 1 all clones had inserts derived from the same part of sbi, suggesting that the encoded protein has only one IgG-binding domain. From the sequences of the binding clones in FIG. 1, the minimal IgG-binding domain is deduced to consist of 52 amino acids.

Example 3

Analysis of the Immunoglobulin Specificity of Protein Sbi

To determine the specificity of protein Sbi, a phage-stock was prepared as described above from clone Ig4, encoding the IgG-binding domain of protein Sbi (Jacobsson & Frykberg, 1995). The stock was diluted to $10^8$ phagemid particles ml⁻¹ and 100 μl was panned as described (Jacobsson & Frykberg, 1995) against human IgG, IgM, IgA, IgG3κ, IgG3λ as well as IgG from rat, goat, pig, cow, sheep, horse, guinea pig, dog, rabbit and chicken (Sigma), immobilized in microwells at a concentration of 50 μg ml⁻¹. BSA was included as a negative control. The number of bound phagemid particles was determined as c.f.u. after infection of E. coli TG1 cells with the phage eluated at pH 2.

To analyse the Ig-binding properties of protein Sbi, clone Ig4 encoding the IgG-binding domain, was used to produce phage-particles displaying the binding domain on the surface. These phages were panned against different immunoglobulins and the number of binding phagemid-particles was determined and used as a measure of the binding ability (FIG. 3).

Example 4

Protein Purification and Electrophoresis

The MAL-fusion proteins, MAL-Sbi (aa 33–436, SEQ ID NO:3) and MAL-SbiΔ(aa 143–436, SEQ ID NO:4), were purified from E. coli lysates on an amylose-resin according to the manufacturer's instructions (New England Biolabs). MAL-Sbi was further purified on IgG-Sepharose® according to the manufacturer's instructions (Pharmacia Biotech).

Antibodies against protein Sbi, developed in chickens, were obtained through Immunsystem AB (Uppsala, Sweden) (four immunizations of 50 μg MAL-SbiΔ-protein). The antibodies were affinity-purified on immobilized MAL-SbiΔ-protein and labelled with Horse-radish peroxidase (HRP) (Boehringer Mannheim). Commercially available HRP-labelled chicken antibodies against protein A were ordered from Immunsystem AB.

To further characterize the protein encoded by the sbi-gene the Pst1-XbaI fragment from pPX1, encoding the complete protein, was made blunt ended and inserted into the Sma1 site in the shuttle plasmid pBR473. The construct, pShPX1, was first introduced into the restriction negative S. aureus strain 113 and plasmid DNA was prepared from one chloramphenicol resistant colony. The plasmid was then transferred to S. epidermidis strain 247, known to be negative in IgG-binding as all coagulase negative staphyolococci, and chloramphenicol resistant colonies were screened for binding of HRP-labeled IgG. All clones analysed had recieved IgG-binding capacity and one of the clones, SePX1, was chosen for further studies. Chromosomal DNA was prepared from this clone, cleaved with SnaBI and HindIII and analysed by Southern blot hybridization, which showed that the clone contained the sbi gene as expected (data not shown).

The bacterial cells in over night-cultures of Newman 4 (2 ml), Cowan 1 (2 ml) and S. epidermidis containing pShPX1 (40 ml) were collected by centrifugation and washed once in PBS (phosphate buffered saline pH 7.4). Newman 4- and S. epidermidis-cells were resuspensed in 40 μl PBS followed by addition of 40 μl 2×sample-buffer (1×buffer=125 mM Tris-HCI pH 6.8, 10% glycerol, 5% (v/v) β-mercaptoethanol, 2% SDS and 0.1% bromophenol blue) and the samples boiled for 2 minutes. To release protein A, the same amount of cells in PBS was treated with lysostaphin (0.1 mg/ml, Sigma) for 5 minutes at 37° C. before addition of the sample-buffer and boiling for 2 minutes. The 1 μl of the samples were analyzed by SDS-PAGE using the Phast-system (Pharmacia Biotech). Also included were 1/40 μg protein A (Pharmacia Biotech), 1/20 μg MAL-Sbi (SEQ ID NO:3) and 1/20 μg MAL-SbiΔ (SEQ ID NO:4). The proteins were blotted onto nitrocellulose-filters (Schleicher & Schuell) and proteins detected using HRP-labelled affinity purified rabbit anti-chicken (diluted 1/500, Sigma), anti-Sbi (10 μg/ml) or anti-protein A (15 μg/ml). Bound antibodies were detected using 4-chloro-1-naphtol (Serva).

To further characterize the protein encoded by the sbi-gene, two clones were made in the pMAL-c2 vector, expressing the mature full length protein (MAL-Sbi, aa 33–436, SEQ ID NO:3) and a truncated protein (MAL-SbiΔ, aa 143–436, SEQ ID NO:4) lacking the known IgG-binding domain. The purified products were analysed by SDS-PAGE and Western blot together with commercially available protein A, cell surface extract of S. epidermidis containing pShX1 and S. aureus Newman 4, as well as lysed Newman 4 and Cowan I cells. Three duplicate gels were blotted onto nitrocellulose-filters and the blots developed with HRP-labelled rabbit IgG for detection of protein A and Sbi. anti-protein A and anti-Sbi, respectively.

Western blot analysis of purified proteins shows that antibodies against MAL-SbiΔ (SEQ ID NO:4) recognise both MAL-Sbi (SEQ ID NO:3)and MAL-SbiΔ (SEQ ID NO:4) but not protein A. Commercially available antibodies against protein A (Immunsystem AB, Uppsala) recognise both protein A and MAL-Sbi but not Mal-SbiΔ. This means that the antibodies against protein A recognise the IgG-binding domain in protein Sbi. The antibodies against the polypeptide fragment MAL-SbiΔ of the protein Sbi are specific for the protein Sbi. Western blot analysis of lysates of two different S. aureus strains show that the antibodies against MAL-SbiΔ (SEQ ID NO:4) only recognise protein Sbi and no other staphylococcal protein.

Example 5

Occurence of the sbi-gene in Staphylococcal Strains

Chromosomal DNA was isolated from S. aureus strains 8325-4, Cowan I, Newman 4 and Wood 46. The DNAs were digested with the enzyme HindIII followed by agarose gel electrophoresis and then blotted onto a nitrocellulose filter. The Southern blot shows that the sbi-gene is present in all four *S. aureus* strains tested.

Example 6

Purification of Apolipoprotein H

Purified MAL-SbiΔ (SEQ ID NO:4) was immobilised on CNBr-activated Sepharose® (Pharmacia Biotech) according to the manufacturer's instruction. Ten ml rat (ICN), bovine (Life Technologies) or human (Uppsala university hospital) serum was diluted 20 times in PBS and passed over the column. After extensive washing with acetate-buffer pH 5.5, the bound protein was eluted in acetate buffer pH 2.7. The eluate was lyophilised and the protein dissolved in water.

The proteins were analysed by SDS-PAGE and blotted onto nitrocellulose-filters (Schleisher-Schuell) together with commercially available human apolipoprotein H (ICN). The proteins were detected with rabbit anti-human apolipoprotein H antibodies (Chemicon) and HRP-labelled goat anti-rabbit antibodies (Santa Cruz Biotechnology). An identical Western blot was treated with purified MAL-Sbi after which HRP-labelled chicken antibodies against protein Sbi was added. Both filters were developed with 4-chloro-1-naphtol.

These results show that in addition to IgG, protein Sbi binds apolipoprotein H from various mammals and that it can be used for purification of apolipoprotein H.

Example 7

Purification of Apolipoprotein H, and Immunsation with Protein Fragments

Apolipoprotein H from human and bovine sera were also purified on SbiApoB (aa 145–267, SEQ ID NO:6). This domain is used for immunisation in different animals (rat and guinea pig) to investigate if it confers protection against *S. aureus* infections. The recombinant protein SbiIgGB (31–150, SEQ ID NO:5) is also included in this immunisation study.

The Impact™ T7-system from New England Biolabs was used for construction and purification of SbiIgGB (aa 31–150, SEQ ID NO:5) and SbiApoB (aa 145–267, SEQ ID NO:6). The corresponding parts of the sbi-gene was amplified by PCR using the oligonucleotides IgG1pr (5'-CAT GCC ATG GAA AAC ACG CAA CAA ACT TCA- 3', i.e. SEQ ID NO:19), IgG2pr (5'-TTC TTT AGC TTT AGA AGA-3', i.e. SEQ ID NO:20), Apolpr (5'-CAT GCC ATG GAA TCT TCT AAA GCT AAA GAA CGT- 3', i.e. SEQ ID NO:21) and Abobin (5'-TGG CGC CAC TTT CTT TTC AGC-3', i.e. SEQ ID NO:22). The PCR-products were digested with NcoI and treated with T4 polynucleotide kinase and ligated into the pTYB4 vector. The vector had previously been digested with the NcoI and SmaI and treated with alkaline phosphatase. The constructions were transformed into BL21(DE3)pLysS-cells and protein was then purified according to the manufacturer's instructions.

The purified SbiApoB was coupled to a Hitrap® affinity column (Amersham Pharmacia BioTech). Bovine serum (Life Technologies) was applied onto the column. After extensive washing with PBS (phosphate buffered saline) supplied with 0.05% Tween20, bound protein was eluted in 0.1 M glycine pH 3.0. The purified protein was analysed by SDS-PAGE and Western-blotting and was shown to be recognised by rabbit anti-human apolipoprotein H antibodies (Chemicon).

Example 8

Passive Immunisation with Protein Fragments

As prophylaxis or for treatment of acute infections in a patient, passive immunisation may be effected by administration of antibodies directed against the protein Sbi.

These antibodies can be obtained by immunisation of horses with a dose of 50–1000 μg of the polypeptide fragments SEQ ID NO:4 and/or SEQ ID NO:6 of the protein Sbi, optionally coupled to a carrier, at tree to four separate occasions, followed by purification of the total antibody fraction and/or the specific antibody fraction directed against the non-IgG binding portions of the protein Sbi from serum.

In addition, antibodies can be obtained by immunisation of chickens with 10–100 μg of the polypeptide fragments SEQ ID NO:4 and/or SEQ ID NO:6 of the protein Sbi, optionally coupled to a carrier proteins per immunisation, at 3–4 separate occasions. The specific antibodies against the non-IgG binding portions of the protein Sbi can then be purified from the eggs and used for passive immunisation. Alternatively, the raw eggs can be consumed to give passive protection.

Finally, antibodies can also be isolated from humans that have recovered from a staphylococcal infection by purification of the total antibody fraction and/or the specific antibody fraction directed against the non-IgG binding portions of the protein Sbi from serum.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

References

Boyle, M. D. P. (1990). *Bacterial Immunoglobulin-Binding Proteins*, vols. 1 and 2, London, Academic Press, Inc. (London), Ltd.

Hoogenboom, H. R., Griffiths, A. D., Johnson, K. S., Chiswell, D. J., Hudson, P. & Winter, G. (1991). Multisubunit proteins on the surface of filamentous phage: methodologies for displaying antibody (Fab) heavy and light chains. *Nucl Acids Res* 19, 4133–4137.

Jacobsson, K. & Frykberg, L. (1995). Cloning of ligand-binding domains of bacterial receptors by phage display. *BioTechniques* 18, 878–885

Jönsson, K., McDevitt, D., Homonylo McGavin, M., Patti, J. M. & Höök, M. (1995). Staphylococcus aureus expresses a major histocompatibility complex class II analog. *J. Biol. Chem.* 270,21457–21460.

Lindberg, M., Sjöström, J.-E. & Johansson, T. (1972). Transformation of chromosomal and plasmid characters in *Staphylococcus aureus*. *J Bacteriol* 109, 844–847.

Park, P. W., Rosenbloom, J., Abrams, W. R., Rosenbloom, J. & Mecham, R. P. (1996). Molecular cloning and expression of the gene for elastin-binding protein (ebpS) in *Staphylococcus aureus*. *J. Biol. Chem.* 271, 15803–15809.

Sambrook, J., Fritsch, E. F. & Maniatis, T. (1989). *Molecular Cloning: a Laboratory Manual,* 2nd edn. Cold Spring Harbor, N.Y.: Cold Spring Harbour Laboratory.

Schneewind, O., Fowler, A. & Faull, K. F. (1995). Structure of cell wall anchor of surface proteins in *Staphylococcus aureus*. *Science* 268, 103–106.

Uhlén, M., Guss, B., Nilsson, B., Gatenbeck, S., Philipson, L. & Lindberg, M. (1984). Complete sequence of the staphylococcal gene encoding protein A, a gene evolved through multiple duplications. *J Biol Chem* 259, 1695–1702.

SEQUENCE LISTING

<160> NUMBER OF SEQ ID NOS: 6

<210> SEQ ID NO 1
<211> LENGTH: 1620
<212> TYPE: DNA
<213> ORGANISM: Staphylococcus aureus

<400> SEQUENCE: 1

```
agtacttcct tacttaaaat acgctgaatg ttctgaatta aacgctttt tacatagtta      60
acactagtta atctattagt taacattagt taataattag ttaatttcca tttgtattct    120
catgtgataa attctaaaag catacaataa atttaatatg taaaagaaa gggaatacac     180
atgaaaaata aatatatctc gaagttgcta gttggggcag caacaattac gttagctaca    240
atgatttcaa atggggaagc aaaagcgagt gaaaacacgc aacaaacttc aactaagcac    300
caaacaactc aaaacaacta cgtaacagat caacaaaaag cttttttatca agtattacat   360
ctaaaaggta tcacagaaga acaacgtaac caatacatca aaacattacg cgaacaccca    420
gaacgtgcac aagaagtatt ctctgaatca cttaaagaca gcaagaaccc agaccgacgt    480
gttgcacaac aaaacgcttt ttacaatgtt cttaaaaatg ataacttaac tgaacaagaa    540
aaaaataatt acattgcaca aattaaagaa aaccctgata gaagccaaca agtttgggta    600
gaatcagtac aatcttctaa agctaaagaa cgtcaaaata ttgaaaatgc ggataaagca    660
attaaagatt ccaagataa caaagcacca cacgataaat cagcagcata tgaagctaac    720
tcaaaattac ctaaagattt acgtgataaa aacaaccgct ttgtagaaaa agtttcaatt    780
gaaaaagcaa tcgttcgtca tgatgagcgt gtgaaatcag caaatgatgc aatctcaaaa    840
ttaaatgaaa aagattcaat tgaaaacaga cgtttagcac aacgtgaagt taacaaagca    900
cctatggatg taaagagca tttacagaaa caattagacg cattagttgc tcaaaaagat    960
gctgaaaaga agtggcgcc aaaagttgag gctcctcaaa ttcaatcacc acaaattgaa   1020
aaacctaaag tagaatcacc aaaagttgaa gtccctcaaa ttcaatcacc aaaagttgag   1080
gttcctcaat ctaaattatt aggttactac caatcattaa agattcatt taactatggt   1140
tacaagtatt taacagatac ttataaagc tataaagaaa aatatgatac agcaaagtac   1200
tactataata cgtactataa atacaaaggt gcgattgatc aaacagtatt aacagtacta   1260
ggtagtggtt ctaaatctta catccaacca ttgaaagttg atgataaaaa cggctactta   1320
gctaaatcat atgcacaagt aagaaactat gtaactgagt caatcaatac tggtaaagta   1380
ttatatactt tctaccaaaa cccaacatta gtaaaaacag ctattaaagc tcaagaaact   1440
gcatcatcaa tcaaaatac attaagtaat ttattatcat tctggaaata atcaatcaaa   1500
aatatcttct ctagttttac atcattttt aaataatttt cgtaacaaac cgtgattaaa   1560
aagaaccgtt gattctcaat cgaatctacg gttctttttt cattttccat caattaaatg   1620
```

<210> SEQ ID NO 2
<211> LENGTH: 436
<212> TYPE: PRT
<213> ORGANISM: Staphylococcus aureus

<400> SEQUENCE: 2

```
Met Lys Asn Lys Tyr Ile Ser Lys Leu Leu Val Gly Ala Ala Thr Ile
 1               5                  10                  15

Thr Leu Ala Thr Met Ile Ser Asn Gly Glu Ala Lys Ala Ser Glu Asn
            20                  25                  30
```

```
Thr Gln Gln Thr Ser Thr Lys His Gln Thr Thr Gln Asn Asn Tyr Val
         35                  40                  45
Thr Asp Gln Gln Lys Ala Phe Tyr Gln Val Leu His Leu Lys Gly Ile
     50                  55                  60
Thr Glu Glu Gln Arg Asn Gln Tyr Ile Lys Thr Leu Arg Glu His Pro
 65                  70                  75                  80
Glu Arg Ala Gln Glu Val Phe Ser Glu Ser Leu Lys Asp Ser Lys Asn
                 85                  90                  95
Pro Asp Arg Arg Val Ala Gln Gln Asn Ala Phe Tyr Asn Val Leu Lys
             100                 105                 110
Asn Asp Asn Leu Thr Glu Gln Glu Lys Asn Asn Tyr Ile Ala Gln Ile
             115                 120                 125
Lys Glu Asn Pro Asp Arg Ser Gln Gln Val Trp Val Glu Ser Val Gln
 130                 135                 140
Ser Ser Lys Ala Lys Glu Arg Gln Asn Ile Glu Asn Ala Asp Lys Ala
 145                 150                 155                 160
Ile Lys Asp Phe Gln Asp Asn Lys Ala Pro His Asp Lys Ser Ala Ala
             165                 170                 175
Tyr Glu Ala Asn Ser Lys Leu Pro Lys Asp Leu Arg Asp Lys Asn Asn
             180                 185                 190
Arg Phe Val Glu Lys Val Ser Ile Glu Lys Ala Ile Val Arg His Asp
             195                 200                 205
Glu Arg Val Lys Ser Ala Asn Asp Ala Ile Ser Lys Leu Asn Glu Lys
             210                 215                 220
Asp Ser Ile Glu Asn Arg Arg Leu Ala Gln Arg Glu Val Asn Lys Ala
 225                 230                 235                 240
Pro Met Asp Val Lys Glu His Leu Gln Lys Gln Leu Asp Ala Leu Val
             245                 250                 255
Ala Gln Lys Asp Ala Glu Lys Lys Val Ala Pro Lys Val Glu Ala Pro
             260                 265                 270
Gln Ile Gln Ser Pro Gln Ile Glu Lys Pro Lys Val Glu Ser Pro Lys
             275                 280                 285
Val Glu Val Pro Gln Ile Gln Ser Pro Lys Val Glu Val Pro Gln Ser
 290                 295                 300
Lys Leu Leu Gly Tyr Tyr Gln Ser Leu Lys Asp Ser Phe Asn Tyr Gly
 305                 310                 315                 320
Tyr Lys Tyr Leu Thr Asp Thr Tyr Lys Ser Tyr Lys Glu Lys Tyr Asp
             325                 330                 335
Thr Ala Lys Tyr Tyr Asn Thr Tyr Tyr Lys Tyr Lys Gly Ala Ile
             340                 345                 350
Asp Gln Thr Val Leu Thr Val Leu Gly Ser Gly Ser Lys Ser Tyr Ile
             355                 360                 365
Gln Pro Leu Lys Val Asp Asp Lys Asn Gly Tyr Leu Ala Lys Ser Tyr
 370                 375                 380
Ala Gln Val Arg Asn Tyr Val Thr Glu Ser Ile Asn Thr Gly Lys Val
 385                 390                 395                 400
Leu Tyr Thr Phe Tyr Gln Asn Pro Thr Leu Val Lys Thr Ala Ile Lys
             405                 410                 415
Ala Gln Glu Thr Ala Ser Ser Ile Lys Asn Thr Leu Ser Asn Leu Leu
             420                 425                 430
Ser Phe Trp Lys
 435
```

<210> SEQ ID NO 3
<211> LENGTH: 404
<212> TYPE: PRT
<213> ORGANISM: Staphylococcus aureus

<400> SEQUENCE: 3

Thr Gln Gln Thr Ser Thr Lys His Gln Thr Thr Gln Asn Asn Tyr Val
1               5                   10                  15

Thr Asp Gln Gln Lys Ala Phe Tyr Gln Val Leu His Leu Lys Gly Ile
            20                  25                  30

Thr Glu Glu Gln Arg Asn Gln Tyr Ile Lys Thr Leu Arg Glu His Pro
        35                  40                  45

Glu Arg Ala Gln Glu Val Phe Ser Glu Ser Leu Lys Asp Ser Lys Asn
    50                  55                  60

Pro Asp Arg Arg Val Ala Gln Gln Asn Ala Phe Tyr Asn Val Leu Lys
65                  70                  75                  80

Asn Asp Asn Leu Thr Glu Gln Glu Lys Asn Asn Tyr Ile Ala Gln Ile
                85                  90                  95

Lys Glu Asn Pro Asp Arg Ser Gln Gln Val Trp Val Glu Ser Val Gln
            100                 105                 110

Ser Ser Lys Ala Lys Glu Arg Gln Asn Ile Glu Asn Ala Asp Lys Ala
        115                 120                 125

Ile Lys Asp Phe Gln Asp Asn Lys Ala Pro His Asp Lys Ser Ala Ala
    130                 135                 140

Tyr Glu Ala Asn Ser Lys Leu Pro Lys Asp Leu Arg Asp Lys Asn Asn
145                 150                 155                 160

Arg Phe Val Glu Lys Val Ser Ile Glu Lys Ala Ile Val Arg His Asp
                165                 170                 175

Glu Arg Val Lys Ser Ala Asn Asp Ala Ile Ser Lys Leu Asn Glu Lys
            180                 185                 190

Asp Ser Ile Glu Asn Arg Arg Leu Ala Gln Arg Glu Val Asn Lys Ala
        195                 200                 205

Pro Met Asp Val Lys Glu His Leu Gln Lys Gln Leu Asp Ala Leu Val
    210                 215                 220

Ala Gln Lys Asp Ala Glu Lys Lys Val Ala Pro Lys Val Glu Ala Pro
225                 230                 235                 240

Gln Ile Gln Ser Pro Gln Ile Glu Lys Pro Lys Val Glu Ser Pro Lys
                245                 250                 255

Val Glu Val Pro Gln Ile Gln Ser Pro Lys Val Glu Val Pro Gln Ser
            260                 265                 270

Lys Leu Leu Gly Tyr Tyr Gln Ser Leu Lys Asp Ser Phe Asn Tyr Gly
        275                 280                 285

Tyr Lys Tyr Leu Thr Asp Thr Tyr Lys Ser Tyr Lys Glu Lys Tyr Asp
    290                 295                 300

Thr Ala Lys Tyr Tyr Asn Thr Tyr Lys Tyr Lys Gly Ala Ile
305                 310                 315                 320

Asp Gln Thr Val Leu Thr Val Leu Gly Ser Gly Ser Lys Ser Tyr Ile
                325                 330                 335

Gln Pro Leu Lys Val Asp Asp Lys Asn Gly Tyr Leu Ala Lys Ser Tyr
            340                 345                 350

Ala Gln Val Arg Asn Tyr Val Thr Glu Ser Ile Asn Thr Gly Lys Val
        355                 360                 365

Leu Tyr Thr Phe Tyr Gln Asn Pro Thr Leu Val Lys Thr Ala Ile Lys
    370                 375                 380

Ala Gln Glu Thr Ala Ser Ser Ile Lys Asn Thr Leu Ser Asn Leu Leu
385                 390                 395                 400

Ser Phe Trp Lys

<210> SEQ ID NO 4
<211> LENGTH: 294
<212> TYPE: PRT
<213> ORGANISM: Staphylococcus aureus

<400> SEQUENCE: 4

Val Gln Ser Ser Lys Ala Lys Glu Arg Gln Asn Ile Glu Asn Ala Asp
 1               5                  10                  15

Lys Ala Ile Lys Asp Phe Gln Asp Asn Lys Ala Pro His Asp Lys Ser
             20                  25                  30

Ala Ala Tyr Glu Ala Asn Ser Lys Leu Pro Lys Asp Leu Arg Asp Lys
         35                  40                  45

Asn Asn Arg Phe Val Glu Lys Val Ser Ile Glu Lys Ala Ile Val Arg
     50                  55                  60

His Asp Glu Arg Val Lys Ser Ala Asn Asp Ala Ile Ser Lys Leu Asn
 65                  70                  75                  80

Glu Lys Asp Ser Ile Glu Asn Arg Arg Leu Ala Gln Arg Glu Val Asn
                 85                  90                  95

Lys Ala Pro Met Asp Val Lys Glu His Leu Gln Lys Gln Leu Asp Ala
            100                 105                 110

Leu Val Ala Gln Lys Asp Ala Glu Lys Lys Val Ala Pro Lys Val Glu
        115                 120                 125

Ala Pro Gln Ile Gln Ser Pro Gln Ile Glu Lys Pro Lys Val Glu Ser
    130                 135                 140

Pro Lys Val Glu Val Pro Gln Ile Gln Ser Pro Lys Val Glu Val Pro
145                 150                 155                 160

Gln Ser Lys Leu Leu Gly Tyr Tyr Gln Ser Leu Lys Asp Ser Phe Asn
                165                 170                 175

Tyr Gly Tyr Lys Tyr Leu Thr Asp Thr Tyr Lys Ser Tyr Lys Glu Lys
            180                 185                 190

Tyr Asp Thr Ala Lys Tyr Tyr Asn Thr Tyr Lys Tyr Lys Gly
        195                 200                 205

Ala Ile Asp Gln Thr Val Leu Thr Val Leu Gly Ser Gly Ser Lys Ser
    210                 215                 220

Tyr Ile Gln Pro Leu Lys Val Asp Asp Lys Asn Gly Tyr Leu Ala Lys
225                 230                 235                 240

Ser Tyr Ala Gln Val Arg Asn Tyr Val Thr Glu Ser Ile Asn Thr Gly
                245                 250                 255

Lys Val Leu Tyr Thr Phe Tyr Gln Asn Pro Thr Leu Val Lys Thr Ala
            260                 265                 270

Ile Lys Ala Gln Glu Thr Ala Ser Ser Ile Lys Asn Thr Leu Ser Asn
        275                 280                 285

Leu Leu Ser Phe Trp Lys
    290

<210> SEQ ID NO 5
<211> LENGTH: 120
<212> TYPE: PRT
<213> ORGANISM: Staphylococcus aureus

<400> SEQUENCE: 5

```
Glu Asn Thr Gln Gln Thr Ser Thr Lys His Gln Thr Thr Gln Asn Asn
 1               5                  10                  15

Tyr Val Thr Asp Gln Gln Lys Ala Phe Tyr Gln Val Leu His Leu Lys
                 20                  25                  30

Gly Ile Thr Glu Glu Gln Arg Asn Gln Tyr Ile Lys Thr Leu Arg Glu
             35                  40                  45

His Pro Glu Arg Ala Gln Glu Val Phe Ser Glu Ser Leu Lys Asp Ser
         50                  55                  60

Lys Asn Pro Asp Arg Arg Val Ala Gln Gln Asn Ala Phe Tyr Asn Val
 65                  70                  75                  80

Leu Lys Asn Asp Asn Leu Thr Glu Gln Glu Lys Asn Asn Tyr Ile Ala
                 85                  90                  95

Gln Ile Lys Glu Asn Pro Asp Arg Ser Gln Gln Val Trp Val Glu Ser
            100                 105                 110

Val Gln Ser Ser Lys Ala Lys Glu
            115                 120

<210> SEQ ID NO 6
<211> LENGTH: 123
<212> TYPE: PRT
<213> ORGANISM: Staphylococcus aureus

<400> SEQUENCE: 6

Ser Ser Lys Ala Lys Glu Arg Gln Asn Ile Glu Asn Ala Asp Lys Ala
 1               5                  10                  15

Ile Lys Asp Phe Gln Asp Asn Lys Ala Pro His Asp Lys Ser Ala Ala
                 20                  25                  30

Tyr Glu Ala Asn Ser Lys Leu Pro Lys Asp Leu Arg Asp Lys Asn Asn
             35                  40                  45

Arg Phe Val Glu Lys Val Ser Ile Glu Lys Ala Ile Val Arg His Asp
         50                  55                  60

Glu Arg Val Lys Ser Ala Asn Asp Ala Ile Ser Lys Leu Asn Glu Lys
 65                  70                  75                  80

Asp Ser Ile Glu Asn Arg Arg Leu Ala Gln Arg Glu Val Asn Lys Ala
                 85                  90                  95

Pro Met Asp Val Lys Glu His Leu Gln Lys Gln Leu Asp Ala Leu Val
            100                 105                 110

Ala Gln Lys Asp Ala Glu Lys Lys Val Ala Pro
            115                 120
```

What is claimed is:

1. Isolated or purified protein expressed by a bacterium of the genus *Staphylococcus aureus* or an immunogenic or antigenic polypeptide fragment of said protein comprising at least 15 amino acid residues other than the 84 aa fragment at the position 38–121, which protein comprises the amino acid sequence SEQ ID NO: 2

```
Met Lys Asn Lys Tyr Ile Ser Lys Leu Leu Val Gly
 1               5                  10

Ala Ala Thr Ile Thr Leu Ala Thr Met Ile Ser Asn
                 15                  20

Gly Glu Ala Lys Ala Ser Glu Asn Thr Gln Gln Thr
 25                  30                  35

Ser Thr Lys His Gln Thr Thr Gln Asn Asn Tyr Val
             40                  45

Thr Asp Gln Gln Lys Ala Phe Tyr Gln Val Leu His
     50                  55                  60

Leu Lys Gly Ile Thr Glu Glu Gln Arg Asn Gln Tyr
                 65                  70

Ile Lys Thr Leu Arg Glu His Pro Glu Arg Ala Gln
             75                  80

Glu Val Phe Ser Glu Ser Leu Lys Asp Ser Lys Asn
 85                  90                  95

Pro Asp Arg Arg Val Ala Gln Gln Asn Ala Phe Tyr
            100                 105
```

-continued

Asn Val Leu Lys Asn Asp Asn Leu Thr Glu Gln Glu
110             115                 120

Lys Asn Asn Tyr Ile Ala Gln Ile Lys Glu Asn Pro
            125                 130

Asp Arg Ser Gln Gln Val Trp Val Glu Ser Val Gln
        135                 140

Ser Ser Lys Ala Lys Glu Arg Gln Asn Ile Glu Asn
145             150                 155

Ala Asp Lys Ala Ile Lys Asp Phe Gln Asp Asn Lys
            160                 165

Ala Pro His Asp Lys Ser Ala Ala Tyr Glu Ala Asn
170             175                 180

Ser Lys Leu Pro Lys Asp Leu Arg Asp Lys Asn Asn
            185                 190

Arg Phe Val Glu Lys Val Ser Ile Glu Lys Ala Ile
        195                 200

Val Arg His Asp Glu Arg Val Lys Ser Ala Asn Asp
205             210                 215

Ala Ile Ser Lys Leu Asn Glu Lys Asp Ser Ile Glu
            220                 225

Asn Arg Arg Leu Ala Gln Arg Glu Val Asn Lys Ala
        230                 235                 240

Pro Met Asp Val Lys Glu His Leu Gln Lys Gln Leu
            245                 250

Asp Ala Leu Val Ala Gln Lys Asp Ala Glu Lys Lys
            255                 260

Val Ala Pro Lys Val Glu Ala Pro Gln Ile Gln Ser
265             270                 275

Pro Gln Ile Glu Lys Pro Lys Val Glu Ser Pro Lys
            280                 285

Val Glu Val Pro Gln Ile Gln Ser Pro Lys Val Glu
            290                 295                 300

Val Pro Gln Ser Lys Leu Leu Gly Tyr Tyr Gln Ser
                305                 310

Leu Lys Asp Ser Phe Asn Tyr Gly Tyr Lys Tyr Leu
            315                 320

Thr Asp Thr Tyr Lys Ser Tyr Lys Glu Lys Tyr Asp
325             330                 335

Thr Ala Lys Tyr Tyr Tyr Asn Thr Tyr Tyr Lys Tyr
            340                 345

Lys Gly Ala Ile Asp Gln Thr Val Leu Thr Val Leu
            350                 355                 360

Gly Ser Gly Ser Lys Ser Tyr Ile Gln Pro Leu Lys
                365                 370

Val Asp Asp Lys Asn Gly Tyr Leu Ala Lys Ser Tyr
            375                 380

Ala Gln Val Arg Asn Tyr Val Thr Glu Ser Ile Asn
385             390                 395

Thr Gly Lys Val Leu Tyr Thr Phe Tyr Gln Asn Pro
            400                 405

Thr Leu Val Lys Thr Ala Ile Lys Ala Gln Glu Thr
            410                 415                 420

Ala Ser Ser Ile Lys Asn Thr Leu Ser Asn Leu Leu
                425                 430

Ser Phe Trp Lys.
435

2. An immunogenic composition comprising the protein or polypeptide according to claim 1.

\* \* \* \* \*